United States Patent
Fowler

[11] Patent Number: 6,042,572
[45] Date of Patent: Mar. 28, 2000

[54] DEVICE AND METHOD FOR CLEANING ARTIFICIAL BODY PASSAGEWAYS FORMED BETWEEN TWO OPENINGS BY PIERCING

[76] Inventor: Glenda H. Fowler, 463 Old Zebulon Rd., Forsyth, Ga. 31029

[21] Appl. No.: 09/251,852

[22] Filed: Feb. 17, 1999

[51] Int. Cl.$^7$ .................................................. A61M 5/00
[52] U.S. Cl. ..................... 604/239; 604/241; 604/240; 604/272; 604/523
[58] Field of Search ........................ 604/239, 267, 604/272, 523, 240, 241, 38

[56] References Cited

U.S. PATENT DOCUMENTS

| | | | |
|---|---|---|---|
| 634,363 | 10/1899 | Morrison | 604/523 |
| 2,568,207 | 9/1951 | Spicher | 128/329 |
| 3,500,829 | 3/1970 | Abramowitz | 128/215 |
| 3,682,162 | 8/1972 | Colyer | 128/2.1 R |
| 4,041,946 | 8/1977 | Barton | 128/260 |
| 4,240,422 | 12/1980 | Hazen | 128/218 |
| 4,353,370 | 10/1982 | Evans | 128/269 |
| 4,639,252 | 1/1987 | Kelly et al. | 604/282 |
| 4,710,180 | 12/1987 | Johnson | 604/239 |
| 5,141,501 | 8/1992 | Atkinson et al. | 604/269 |
| 5,183,461 | 2/1993 | Hobbs | 604/49 |
| 5,715,850 | 2/1998 | Markgraaf | 132/333 |
| 5,792,099 | 8/1998 | DeCamp et al. | 604/51 |
| 5,819,497 | 10/1998 | Knepper | 604/239 |
| 5,832,971 | 11/1998 | Yale et al. | 141/329 |
| 5,843,043 | 12/1998 | Markus | 604/239 |

*Primary Examiner*—Wynn Wood Coggins
*Assistant Examiner*—Kevin C. Sirmons
*Attorney, Agent, or Firm*—Joseph N. Breaux

[57] ABSTRACT

A hygiene device for cleaning body passageways formed between two openings by piercing. The device includes a syringe assembly and a disposable cleaning tip assembly including a thin, hollow needle shaft that is inserted into the piercing that terminates in a semi-spherical shaft end provided with multiple cleaning orifices. A semi-spherical shaft end is proved to prevent punctures to the walls defining the body passageway. The cleaning method includes the step of simultaneously inserting the semi-spherical shaft end into one of the two openings of the artificial body passageway to be cleaned while depressing the syringe plunger to force cleaning solution out into the artificial body passageway through the multiple cleaning orifices of the semi-spherical shaft end.

3 Claims, 1 Drawing Sheet

6,042,572

DEVICE AND METHOD FOR CLEANING ARTIFICIAL BODY PASSAGEWAYS FORMED BETWEEN TWO OPENINGS BY PIERCING

TECHNICAL FIELD

The present invention relates to cleaning devices and methods and more particularly to a device for cleaning artificial body passageways formed between two openings by piercing that includes a syringe assembly including a syringe body having a cleaning solution chamber formed therein and including a threaded connecting fitting surrounding a syringe tip and a syringe plunger slidably disposed within the cleaning solution chamber; a disposable cleaning tip assembly including a hollow needle shaft having a cleaning solution passageway formed therein and a diameter less than one-thirty-seconds of an inch, a semi-spherical shaft end provided with multiple cleaning orifices in connection with the cleaning solution passageway of the hollow needle shaft, and a screw on tip connecting fitting including two thread engaging projections threadably engaging the threaded connecting fitting of the syringe body and a syringe tip receiving cavity in connection with the cleaning solution passageway of the hollow needle shaft; and a method of cleaning an artificial body passageway formed between two openings by piercing that includes the steps of a) providing a device for cleaning artificial body passageways formed between two openings by piercing that includes a syringe assembly including a syringe body having a cleaning solution chamber formed therein and including a threaded connecting fitting surrounding a syringe tip and a syringe plunger slidably disposed within the cleaning solution chamber; a disposable cleaning tip assembly including a hollow needle shaft having a cleaning solution passageway formed therein and a diameter less than one-thirty-seconds of an inch, a semi-spherical shaft end provided with multiple cleaning orifices in connection with the cleaning solution passageway of the hollow needle shaft, and a screw on tip connecting fitting including two thread engaging projections threadably engaging the threaded connecting fitting of the syringe body and a syringe tip receiving cavity in connection with the cleaning solution passageway of the hollow needle shaft; b) providing a quantity of cleaning solution within the cleaning solution chamber; and c) simultaneously inserting the semi-spherical shaft end into one of the two openings of the artificial body passageway formed between two openings by piercing to be cleaned while depressing the syringe plunger to force clearing solution through the cleaning solution passageway of the hollow needle shaft and out into the artificial body passageway through the multiple cleaning orifices of the semi-spherical shaft end.

BACKGROUND ART

Body piercing has become increasing popular as a form of self expression among some groups of individuals. Each of the body piercing is a small diameter passageway formed through a portion of the body that is open at both ends. A retaining device, such as a post of an earing, is inserted through the passageway to retain an ornament on the body. These passageways can become breeding grounds for bacteria and can become infected if not properly cleaned. It would be a benefit, therefore, to have a device for cleaning the artificial body passageways formed between two openings. It would be a further benefit Go have a method for cleaning artificial body passageways formed between two openings that included use of such a device.

GENERAL SUMMARY DISCUSSION OF INVENTION

It is thus an object of the invention to provide a device for cleaning artificial body passageways formed between two openings by piercing.

It is a further object of the invention to provide a device for cleaning artificial body passageways formed between two openings by piercing that includes a syringe assembly including a syringe body having a cleaning solution chamber formed therein and including a threaded connecting fitting surrounding a syringe tip and a syringe plunger slidably disposed within the cleaning solution chamber; a disposable cleaning tip assembly including a hollow needle shaft having a cleaning solution passageway formed therein and a diameter less than one-thirty-seconds of an inch, a semi-spherical shaft end provided with multiple cleaning orifices in connection with the cleaning solution passageway of the hollow needle shaft, and a screw on tip connecting fitting including two thread engaging projections threadably engaging the threaded connecting fitting of the syringe body and a syringe tip receiving cavity in connection with the cleaning solution passageway of the hollow needle shaft.

It is a still further object of the invention to provide a method for cleaning artificial body passageways formed between two openings by piercing.

It is a still further object of the invention to provide a method for cleaning artificial body passageways formed between two openings by piercing that includes the steps of a) providing a device for cleaning artificial body passageways formed between two openings by piercing that includes a syringe assembly including a syringe body having a cleaning solution chamber formed therein and including a threaded connecting fitting surrounding a syringe tip and a syringe plunger slidably disposed within the cleaning solution chamber; a disposable cleaning tip assembly including a hollow needle shaft having a cleaning solution passageway formed therein and a diameter less than one-thirty-seconds of an inch, a semi-spherical shaft end provided with multiple cleaning orifices in connection with the cleaning solution passageway of the hollow needle shaft, and a screw on tip connecting fitting including two thread engaging projections threadably engaging the threaded connecting fitting of the syringe body and a syringe tip receiving cavity in connection with the cleaning solution passageway of the hollow needle shaft; b) providing a quantity of cleaning solution within the cleaning solution chamber; and c) simultaneously inserting the semi-spherical shaft end into one of the two openings of the artificial body passageway formed between two openings by piercing to be cleaned while depressing the syringe plunger to force cleaning solution through the cleaning solution passageway of the hollow needle shaft and out into the artificial body passageway through the multiple cleaning orifices of the semi-spherical shaft end.

Accordingly, a device for cleaning artificial body passageways formed between two openings by piercing as provided. The device for cleaning artificial body passageways formed between two openings by piercing includes a syringe assembly including a syringe body having a cleaning solution chamber formed therein and including a threaded connecting fitting surrounding a syringe tip and a syringe plunger slidably disposed with. The cleaning solution chamber; a disposable cleaning tip assembly including a hollow needle shaft having a cleaning solution passageway formed therein and a diameter less than one-thirty-seconds of an inch, a semi-spherical shaft end provided with multiple cleaning orifices in connection with the cleaning solution passageway of the hollow needle shaft, and a screw on tip connecting fitting including to thread engaging projections threadably engaging the threaded connecting fitting of the syringe body and a syringe tip receiving cavity in connection with the cleaning solution passageway of the hollow needle shaft.

In another aspect of the invention a method for cleaning artificial body passageways formed between two openings by piercing is provided. The method includes the steps of a) providing a device for cleaning artificial body passageways formed between two openings by piercing that includes a syringe assembly including a syringe body having a cleaning solution chamber formed therein and including a threaded connecting fitting surrounding a syringe tip and a syringe plunger slidably disposed within the cleaning solution chamber; a disposable cleaning tip assembly including a hollow needle shaft having a cleaning solution passageway formed therein and a diameter less than one-thirty-seconds of an inch, a semi-spherical shaft end provided with multiple cleaning orifices in connection with the cleaning solution passageway of the hollow needle shaft, and a screw on tip connecting fitting including two thread engaging projections threadably engaging the threaded connecting fitting of the syringe body and a syringe tip receiving cavity in connection with the cleaning solution passageway of the hollow needle shaft; b) providing a quantity of cleaning solution within the cleaning solution chamber; and c) simultaneously inserting the semi-spherical shaft end into one of the two openings of the artificial body passageway formed between two openings by piercing to be cleaned while depressing the syringe plunger to force cleaning solution through the cleaning solution passageway of the hollow needle shaft and out into the artificial body passageway through the multiple cleaning orifices of the semi-spherical shaft end.

BRIEF DESCRIPTION OF DRAWINGS

For a further understanding of the nature and objects of the present invention, reference should be made to the following detailed description, taken in conjunction with the accompanying drawings, in which like elements are given the same or analogous reference numbers and wherein.

EXEMPLARY MODE FOR CARRYING OUT THE INVENTION

Figure 1:
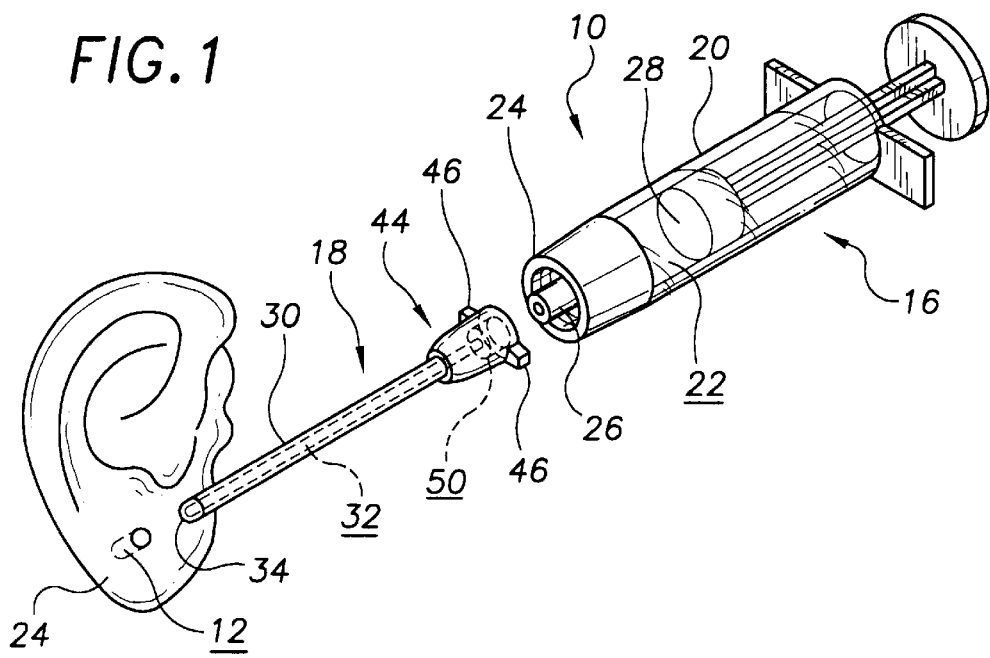
FIG. 1 is an exploded perspective view of an exemplary embodiment of the device for cleaning artificial body passageways formed between two openings by piercing showing The syringe assembly including the syringe body having a cleaning solution chamber formed therein and including a threaded connecting fitting surrounding a syringe tip and a syringe plunger slidably disposed within the cleaning solution chamber; an exemplary disposable cleaning tip assembly including a hollow needle shaft having a cleaning solution passageway formed therein, a semi-spherical shaft. End provided with multiple cleaning orifices in connection with the hollow needle shaft, and a screw on tip connecting fitting including two thread engaging projections threadably engaging the threaded connecting fitting of the syringe body and a syringe tip receiving cavity; and an exemplary artificial, pierced body passageway formed through a representative ear lobe.

FIG. 1 shows an exemplary embodiment of the device For cleaning artificial body passageways formed between two openings by piercing of the present invention, generally designated 10, and an ear lobe 14 having a representative artificial body passageway formed between two openings by piercing 12. Device 10 includes a syringe assembly, generally designated 16, and a disposable cleaning tip assembly, generally designated 18. Syringe assembly 16 is a conventional disposable syringe including a syringe body 20 having a cleaning solution chamber 22 formed therein and a threaded connecting fitting 24 surrounding a syringe tip 26 in connection with the cleaning solution chamber 22; and a syringe plunger 26 slidably disposed within the cleaning solution chamber 22.

Figure 2:
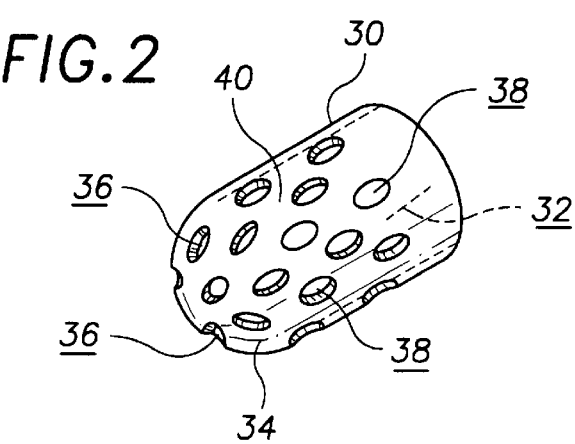
FIG. 2 is a detail perspective view of the semi-spherical shaft end of the exemplary cleaning tip assembly of FIG. 1 showing a portion of she hollow needle shaft integrally formed with formed with the semi-spherical shaft end and a number of the multiple cleaning orifices formed through the semi-spherical shaft end and an end portion of the hollow needle shaft and into connection with the cleaning solution passageway of the hollow needle shaft.

Disposable cleaning tip assembly 18 includes a one-thirty-seconds inch outer diameter, hollow needle shaft 30 having a cleaning solution passageway formed therein 32; a semi-spherical tip end 34, referring now to FIG. 2, having multiple cleaning orifices 36 formed through the exterior thereof into connection with the cleaning solution passageway 32; a number of shaft cleaning orifices 38 formed through the exterior of the shaft end 40 of hollow needle shaft 30; and, referring back to FIG. 1, a screw on tip connecting fitting, generally designated 44, including two thread engaging projections 46 for threadably engaging the threaded connecting fitting 24 of syringe body 20 and a syringe top receiving cavity 50 formed in connection with cleaning solution passageway 32 and sized to frictionally receive syringe tip 26.

Figure 3:
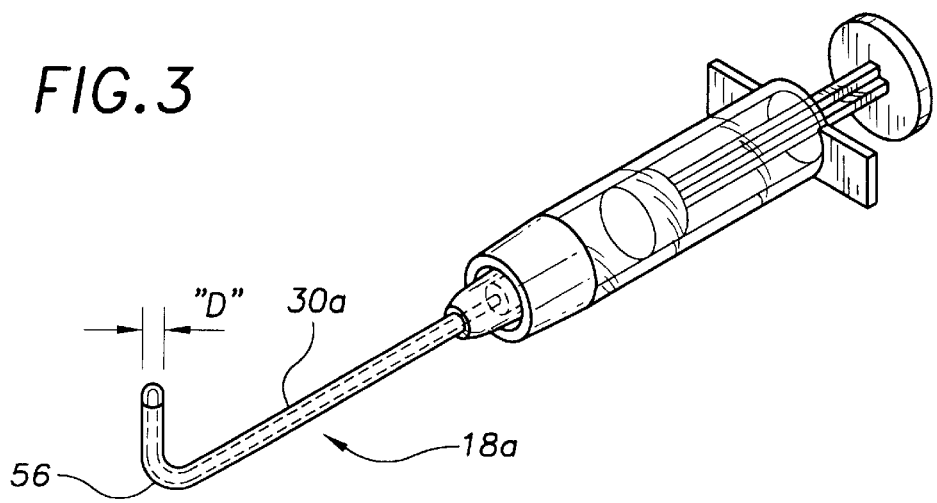
FIG. 3 is a perspective view of a second exemplary embodiment of the device for cleaning artificial body passageways formed between two openings by piercing of the present invention that is identical to the device shown in FIG. 1 except the disposable cleaning tip assembly includes a hollow needle shaft having a cleaning solution passageway formed therein that includes a curved portion.

FIG. 3 shows a second exemplary device 10a that is identical to device 10 of FIG. 1 except a disposable cleaning tip assembly 18a includes a hollow needle shaft 30a having a diameter "D" of one-sixty-fourth of an inch and a ninety degree curved portion 56.

With general reference to FIGS. 1–3, an exemplary method for cleaning an artificial body passageway formed between two openings by piercing 12 includes the steps of a) providing a device for cleaning artificial body passageways formed between two openings by piercing 10 as described herein above; b) providing a quantity of peroxide cleaning solution within the cleaning solution chamber 22; and c) simultaneously inserting the semi-spherical tip end 34 into one of the two openings of artificial body passageway formed between two openings by piercing 12 to be cleaned while depressing syringe plunger 28 to force a quantity of the peroxide cleaning solution through cleaning solution passageway 32 of hollow needle shaft 30 and out into the artificial body passageway 12 through the multiple cleaning orifices 36 of semi-spherical tip end 34.

It can be seen from the preceding description that a device for cleaning artificial body passageways formed between two openings by piercing has been provided that includes a syringe assembly including a syringe body having a cleaning solution chamber formed therein and including a threaded connecting fitting surrounding a syringe tip and a syringe plunger slidably disposed within the cleaning solution chamber; a disposable cleaning tip assembly including a hollow needle shaft having a cleaning solution passageway formed therein and a diameter less than one-thirty-seconds of an inch, a semi-spherical shaft end provided with multiple cleaning orifices in connection with the cleaning solution passageway of the hollow needle shaft, and a screw on tip connecting fitting including two thread engaging projections threadably engaging the threaded connecting fitting of the syringe body and a syringe tip receiving cavity in connection with the cleaning solution passageway of the hollow needle shaft; and a method for cleaning artificial body passageways formed between two openings by piercing has been provided that includes the steps of a) providing a device for cleaning artificial body passageways formed between two openings by piercing that includes a syringe assembly including a syringe body having a cleaning solution chamber formed therein and including a threaded connecting fitting surrounding a syringe tip and a syringe plunger slidably disposed within the cleaning solution chamber; a disposable cleaning tip assembly including a hollow needle shaft having a cleaning solution passageway formed therein and a diameter less than one-thirty-seconds of an inch, a semi-spherical shaft end provided with multiple cleaning orifices in connection with the cleaning solution passageway of the hollow needle shaft, and a screw on tip connecting fitting including two thread engaging projections threadably engaging the threaded connecting fitting of the syringe body and a syringe tip receiving cavity in connection with the cleaning solution passageway of the hollow needle shaft; b) providing a quantity of cleaning solution within the cleaning solution chamber; and c) simultaneously inserting the semi-spherical shaft end into one of the two openings of the artificial body passageway formed between two openings by piercing to be cleaned while depressing the syringe plunger to force cleaning solution through the cleaning solution passageway of the hollow needle shaft and out into the artificial body passageway through the multiple cleaning orifices of the semi-spherical shaft end.

It is noted that the embodiment of the device and method for cleaning artificial body passageways formed between two openings by piercing described herein in detail for exemplary purposes is of course subject to many different variations in structure, design, application and methodology. Because many varying and different embodiments may be made within the scope of the inventive concept(s) herein taught, and because many modifications may be made in the embodiment herein detailed in accordance with the descriptive requirements of the law, it is to be understood that the details herein are to be interpreted as illustrative and not in a limiting sense.

What is claimed is:

1. A device for cleaning artificial body passageways formed between two openings by piercing comprising:
    a syringe assembly including a syringe body having a cleaning solution chamber formed therein and including a threaded connecting fitting surrounding a syringe tip and a syringe plunger slidably disposed within said cleaning solution chamber; a disposable cleaning tip assembly including a hollow needle shaft having a cleaning solution passageway formed therein and a diameter less than one-thirty-seconds of an inch, a shaft end having a semi-spherical tip end, and a screw on tip connecting fitting including two thread engaging projections threadably engaging said threaded connecting fitting of said syringe body and a syringe tip receiving cavity in connection with said cleaning solution passageway of said hollow needle shaft;
    said shaft end being provided with multiple cleaning orifices in connection with said cleaning solution passageway of said hollow needle shaft;
    said tip end having a number of shaft cleaning orifices formed through an exterior thereof.

2. The device and method for cleaning artificial body passageways formed between two openings by piercing of claim 1 wherein:
    said hollow need shaft includes a curved portion between said semi-spherical shaft end and said screw on tip connecting fitting.

3. A method for cleaning artificial body passageways formed between two openings by piercing comprising the steps of:
    a) providing a device for cleaning artificial body passageways formed between two openings by piercing that includes:
        a syringe assembly including a syringe body having a cleaning solution chamber formed therein and including a threaded connecting fitting surrounding a syringe tip and a syringe plunger slidaby disposed within said cleaning solution chamber; and
        a disposable cleaning tip assembly including a hollow needle shaft having a cleaning solution passageway formed therein and a diameter less than one-thirty-seconds of an inch, shaft end having a semi-spherical tip end, and a screw on tip connecting fitting including two thread engaging projections threadably, engaging said threaded connecting fitting of said syringe body and a syringe tip receiving cavity in connection with said cleaning solution passageway of said hollow needle shaft;
        said shaft end being provided with multiple cleaning orifices in connection with said cleaning solution passageway of said hollow needle shaft;
        said tip end having a number of shaft cleaning orifices formed through an exterior thereof;
    b) providing a quantity of cleaning solution within said cleaning solution chamber; and
    c) simultaneously inserting said semi-spherical shaft end into one of the two openings of the artificial body passageway formed between two openings by piercing to be cleaned while depressing said syringe plunger to force cleaning solution through said cleaning solution passageway of said hollow needle shaft and out into the artificial body passageway through said multiple cleaning orifices of said semi-spherical shaft end and said shaft cleaning orifices of said tip end.

* * * * *